US010182924B2

United States Patent
Lechmann et al.

(10) Patent No.: US 10,182,924 B2
(45) Date of Patent: Jan. 22, 2019

(54) PROSTHETIC JOINT WITH ARTICULATING SURFACE LAYERS COMPRISING ADLC

(75) Inventors: Beat Lechmann, Grenchen (CH); Thomas Küenzi, Muttenz (CH); Robert Frigg, Bettlach (CH); Andreas Appenzeller, Biel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 515 days.

(21) Appl. No.: 11/722,905

(22) PCT Filed: Dec. 27, 2005

(86) PCT No.: PCT/CH2005/000777
§ 371 (c)(1),
(2), (4) Date: Jun. 27, 2007

(87) PCT Pub. No.: WO2006/069465
PCT Pub. Date: Jul. 6, 2006

(65) Prior Publication Data
US 2008/0154383 A1    Jun. 26, 2008

(30) Foreign Application Priority Data
Dec. 28, 2004 (CH) .................................. 2160/04

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4425* (2013.01); *A61F 2002/30092* (2013.01);
(Continued)

(58) Field of Classification Search
CPC ............................ A61F 2/4425; A61F 2/4611
(Continued)

(56) References Cited

U.S. PATENT DOCUMENTS 4,759,766 A    7/1988  Buettner-Janz et al.
5,169,597 A    12/1992 Davidson et al. ............ 428/613
(Continued)

FOREIGN PATENT DOCUMENTS

CA    2446934 A1    11/2002
DE    9015697       6/1991
(Continued)

OTHER PUBLICATIONS

International Preliminary Report on Patentability and Written Opinion of the International Searching Authority in appln. No. PCT/CH2005/000777 (Jul. 3, 2007).
(Continued)

*Primary Examiner* — Robert Lynch
(74) *Attorney, Agent, or Firm* — Baker & Hostetler LLP

(57) ABSTRACT

The prosthetic joint has at least two members having each a cooperating articulating surface layer on a substrate material. At least one of said articulating surface layers comprises amorphous diamond-like carbon; or Titanium Nitrate (TiN) on a bonding layer bonded to the substrate material. The prosthetic joint provides a reduction of the number of wear debris and shows enhanced dry run properties.

10 Claims, 3 Drawing Sheets

(52) U.S. Cl.
CPC .............. *A61F 2002/30125* (2013.01); *A61F 2002/30133* (2013.01); *A61F 2002/30382* (2013.01); *A61F 2002/30601* (2013.01); *A61F 2002/30616* (2013.01); *A61F 2002/30649* (2013.01); *A61F 2002/30841* (2013.01); *A61F 2002/443* (2013.01); *A61F 2002/4627* (2013.01); *A61F 2210/0014* (2013.01); *A61F 2220/0033* (2013.01); *A61F 2230/0008* (2013.01); *A61F 2230/0015* (2013.01); *A61F 2310/00023* (2013.01); *A61F 2310/00029* (2013.01); *A61F 2310/0058* (2013.01); *A61F 2310/00179* (2013.01); *A61F 2310/00748* (2013.01)

(58) Field of Classification Search
USPC .......... 623/17.11, 17.14, 17.15, 17.16, 7.141
See application file for complete search history.

(56) References Cited

U.S. PATENT DOCUMENTS

| | | | |
|---|---|---|---|
| 5,314,477 A | 5/1994 | Marnay | |
| 5,458,643 A | 10/1995 | Oka et al. | |
| 5,534,029 A | 7/1996 | Shima | |
| 5,593,719 A | 1/1997 | Dearnaley et al. | |
| 5,688,557 A | 11/1997 | Lemelson et al. | |
| 5,702,448 A | 12/1997 | Buechel et al. | |
| 5,716,415 A | 2/1998 | Steffee | |
| 5,855,996 A * | 1/1999 | Corrigan et al. | 428/212 |
| 5,895,428 A * | 4/1999 | Berry | 623/17.15 |
| 6,083,570 A * | 7/2000 | Lemelson et al. | 427/554 |
| 6,086,593 A | 7/2000 | Bonutti | |
| 6,099,531 A | 8/2000 | Bonutti | |
| 6,368,351 B1 | 4/2002 | Glenn et al. | |
| 6,398,815 B1 | 6/2002 | Pope et al. | |
| 6,419,705 B1 | 7/2002 | Erickson | |
| 6,423,419 B1 | 7/2002 | Teer et al. | |
| 6,447,295 B1 | 9/2002 | Kumar et al. | |
| 6,497,727 B1 | 12/2002 | Pope et al. | |
| 6,514,289 B1 * | 2/2003 | Pope et al. | 623/23.6 |
| 6,527,804 B1 | 3/2003 | Gauchet et al. | |
| 6,579,320 B1 | 6/2003 | Gauchet et al. | |
| 6,596,225 B1 | 7/2003 | Pope et al. | |
| 6,719,794 B2 | 4/2004 | Gerber et al. | |
| 6,852,126 B2 | 2/2005 | Ahlgren | |
| 6,936,071 B1 | 8/2005 | Marnay et al. | |
| 7,083,651 B2 | 8/2006 | Diaz et al. | |
| 7,137,997 B2 | 11/2006 | Paul | |
| 7,364,589 B2 | 4/2008 | Eisermann | |
| 7,494,507 B2 | 2/2009 | Dixon et al. | |
| 7,591,852 B2 | 9/2009 | Prosser | |
| 7,621,956 B2 | 11/2009 | Paul et al. | |
| 2001/0024737 A1 | 9/2001 | Utsumi et al. | |
| 2002/0016635 A1 | 2/2002 | Despres et al. | |
| 2002/0082693 A1 | 6/2002 | Ahlgren | |
| 2003/0074073 A1 * | 4/2003 | Errico et al. | 623/17.14 |
| 2003/0093154 A1 | 5/2003 | Estes et al. | |
| 2003/0191533 A1 | 10/2003 | Dixon et al. | |
| 2003/0195631 A1 | 10/2003 | Ferree | |
| 2003/0220649 A1 | 11/2003 | Bao et al. | |
| 2004/0049280 A1 | 3/2004 | Cauthen | |
| 2004/0059421 A1 | 3/2004 | Glenn | |
| 2004/0088052 A1 | 5/2004 | Dearnaley | |
| 2004/0111159 A1 | 6/2004 | Pope et al. | |
| 2004/0133278 A1 | 7/2004 | Marino et al. | |
| 2004/0158254 A1 | 8/2004 | Eisermann | |
| 2004/0186585 A1 | 9/2004 | Feiwell | |
| 2004/0225365 A1 | 11/2004 | Eisermann et al. | |
| 2004/0225366 A1 | 11/2004 | Eisermann et al. | |
| 2004/0243240 A1 | 12/2004 | Beaurain et al. | |
| 2004/0243241 A1 | 12/2004 | Istephanous et al. | |
| 2005/0021144 A1 | 1/2005 | Malberg et al. | |
| 2005/0033438 A1 | 2/2005 | Schultz et al. | |
| 2005/0038516 A1 | 2/2005 | Spoonamore | |
| 2005/0043800 A1 | 2/2005 | Paul et al. | |
| 2005/0043802 A1 | 2/2005 | Eisermann et al. | |
| 2005/0060036 A1 | 3/2005 | Schultz | |
| 2005/0070900 A1 | 3/2005 | Serhan et al. | |
| 2005/0080488 A1 | 4/2005 | Schultz | |
| 2005/0085917 A1 | 4/2005 | Marnay et al. | |
| 2005/0149194 A1 | 7/2005 | Ahlgren | |
| 2005/0165485 A1 | 7/2005 | Trieu | |
| 2005/0192671 A1 | 9/2005 | Bao et al. | |
| 2005/0197702 A1 | 9/2005 | Coppes et al. | |
| 2005/0216081 A1 * | 9/2005 | Taylor | 623/17.11 |
| 2005/0228500 A1 | 10/2005 | Kim et al. | |
| 2005/0251261 A1 | 11/2005 | Peterman | |
| 2005/0288788 A1 | 12/2005 | Dougherty-Shah | |
| 2006/0004458 A1 | 1/2006 | Collins et al. | |
| 2006/0036261 A1 | 2/2006 | McDonnell | |
| 2006/0229724 A1 | 10/2006 | Lechmann et al. | |
| 2006/0229725 A1 | 10/2006 | Lechmann et al. | 623/17.11 |
| 2007/0032877 A1 * | 2/2007 | Whiteside | 623/22.15 |
| 2007/0198096 A1 | 8/2007 | Wort | |
| 2007/0299521 A1 | 12/2007 | Glenn et al. | |
| 2008/0103597 A1 | 5/2008 | Lechmann et al. | |

FOREIGN PATENT DOCUMENTS

| | | |
|---|---|---|
| DE | 4102509 | 7/1992 |
| DE | 101 08 344 A1 | 9/2001 |
| DE | 20311400 | 10/2003 |
| DE | 20315611 | 12/2003 |
| DE | 10323363 A1 | 12/2004 |
| EP | 0302717 | 2/1989 |
| EP | 0 672 763 A | 9/1995 |
| EP | 0 672 763 A | 9/2001 |
| JP | 60-116361 A | 6/1985 |
| JP | 61-122859 | 6/1986 |
| JP | 02-286158 A | 11/1990 |
| JP | 3-64142 | 10/1991 |
| JP | 06-178787 A | 6/1994 |
| JP | 07-178127 | 7/1995 |
| JP | 09-173437 | 7/1997 |
| JP | 11-318960 A | 11/1999 |
| JP | 2000-087961 | 3/2000 |
| JP | 2001-178813 A | 7/2001 |
| JP | 2001-316800 A | 11/2001 |
| JP | 2002-204825 A | 7/2002 |
| JP | 2004-130077 A | 4/2004 |
| JP | 2004-515311 | 5/2004 |
| JP | 2004-525702 | 8/2004 |
| JP | 2005-505315 | 2/2005 |
| JP | 2005-537065 | 12/2005 |
| JP | 2006-517453 | 7/2006 |
| JP | 2006-528540 | 12/2006 |
| JP | 2007-505669 | 3/2007 |
| JP | 2008-525130 | 7/2008 |
| KR | 0153410 | 11/1998 |
| WO | 95/26697 A1 | 10/1995 |
| WO | 96/04862 A1 | 2/1996 |
| WO | 99/58167 A1 | 11/1999 |
| WO | 01/01893 | 1/2001 |
| WO | 01/54561 A2 | 8/2001 |
| WO | 01/54612 A2 | 8/2001 |
| WO | 01/64142 A1 | 9/2001 |
| WO | 02/05733 A1 | 1/2002 |
| WO | 03/59212 | 7/2003 |
| WO | 20041041131 A2 | 5/2004 |
| WO | 20041056289 A2 | 7/2004 |
| WO | 20041071344 A2 | 8/2004 |
| WO | 20051027799 A1 | 3/2005 |
| WO | 20051107656 A1 | 11/2005 |
| WO | 20061058281 A2 | 6/2006 |
| WO | 20061069465 A1 | 7/2006 |

OTHER PUBLICATIONS

U.S. Appl. No. 11/338,454—"Amendment in Response to the Office Action dated Nov. 17, 2009".
U.S. Appl. No. 11/338,454—USPTO: Final Office Action dated Jun. 8, 2010.

(56) References Cited

OTHER PUBLICATIONS

U.S. Appl. No. 11/338,454—"Request for Continued Examination and Amendment in Response to the Final Office Action dated Jun. 8, 2010".
International Search Report, dated Mar. 20, 2006, in International patent appln. No. PCT/CH2005/000777.
Yoshino et al., Surface and Coatings Technology, 47, 84-88, 1991.
Wei et al., International Materials Reviews, 2000, 45, 133-164.
Watkins, Postlateral fusion of the lumbar and lumbosacral spine, J. Bone Joint Surg. Am, 35-A(4), Oct. 1953, 1014-8.
Watkins, Posterolateral fusion in pseudoarthrosis and posterior element defects of the lumbosacral spine, Clin. Orthop. Relat. Res., 35:80-5, Jul.-Aug. 1964.
Ullmann's encyclopedia of industrial chemistry, vol. A26, 5th completely rev. ed., 1995, Thin Films, 717-725.
Standard Specification for Unalloyed Titanium, for Surgical Implant Applications (UNS R50250, UNS R50400, UNS R50550, UNS 50700), Designation F67-00.
Ronkainen et al., Surface and Coatings Technology, 90, 1997, 190-196.
Pappas et al, Clinical Orthopaedics, 1995, 317, 64-70.
Monteiro et al., Proceedings of the 17th International Conference of the Application of Accelerators in Research and Industry CAARI 2002, pp. 1-7.
Matsuno et al., Biomaterials, 2001, 22, 1253-1262.
Lappalaien et al., Diamond and Related Materials, 1998, 7, 482-485.
Fisher et al., Proc Instn Mech Engrs vol. 216, Part H: J Engineering in Medicine, 2002, 219-230.

\* cited by examiner

PROSTHETIC JOINT WITH ARTICULATING SURFACE LAYERS COMPRISING ADLC

CROSS REFERENCE TO RELATED APPLICATION

This Application is a national stage application under 35 U.S.C. 371 based on International Application Serial No. PCT/CH/2005/000777 filed on Dec. 27, 2005 for "PROSTHETIC JOINT WITH ARTICULATING SURFACE LAYERS COMPRISING ADLC".

FIELD OF THE INVENTION

The invention relates to prosthetic joint with at least two members having each a cooperating articulating surface layer and wherein at least one of said articulating surface layers contains amorphous diamond-like carbon. ("ADLC").

DESCRIPTION OF THE PRIOR ART

The design of the articulating components of orthopedic joint prosthesis is usually based on a ball and socket joint. Due to friction between the articulating components, wear debris is caused. Special hardlayer coatings have been used in the past to try and reduce these wear debris. However, these efforts were only partly successful. Hardlayer coatings as such are well known in techniques where friction and wear debris has to be reduced such as automotive industry, power stations (turbine and generator design) or valve control in engines for cars.

From U.S. Pat. No. 6,398,815 B1 POPE ET AL. a prosthetic joint is known with a superhard articulation surface consisting of poly-crystalline diamond-like carbon.

The disadvantage of poly-crystalline diamond lies in the fact that it is produced at high temperatures where the mechanical integrity of the substrate is not guaranteed anymore. Furthermore, the initial surface of poly-crystalline diamond is rough which requires a final polishing process step.

From U.S. Pat. No. 6,447,295 KUMAR ET AL an ADLC coated dental retaining screw is known. KUMAR discloses the application of ADLC against cold welding between titanium implants. The application of the hard layer on the substantial more elastic substrate bears the risk of exfoliation, i.e. the destruction of the hard layer. The coating of KUMAR would not be suitable for an articulation surface.

It is further known from US 2005/0016635 DESPRES III ET AL. to use ADLC for a knee-endoprosthesis; however, the ADLC surface is explicitly used as a coating for promoting tissue in-growth or on-growth to that surface and not for an articulating surface of a an endo-joint prosthesis

SUMMARY OF THE INVENTION

Metal-on-Metal articulation in endo-joint prosthesis create wear debris, in particular small particles of Chromium, Cobalt and Molybdenum which will be released from the surface. Therefore it is an object of the invention to provide a prosthetic joint having articulating surfaces which lead to a reduction of the number of such released particles.

Another object of this invention is to provide a prosthetic joint with enhanced dry run properties.

Further objects of this invention are to provide a prosthetic joint having:

higher biological compatibility; and
lower risk of delamination of the hard layer from the substrate.

The prosthetic joints with the ADLC surface layers according to the invention have shown excellent properties particularly under dry run conditions. The friction factor is reduced as well, which leads to lower volume of wear debris.

ADLC is processed at temperatures between 150 and 250° C. At these temperatures the usual substrates CoCrMo and CoCrMoC do not change its material structure and remain in sound condition. No final polishing is necessary due to the fact that ADLC and its bonding layer is applied literally atom by atom, i.e. not changing the surface topography.

In a special embodiment said amorphous diamond-like carbon is tetrahedral amorphous diamond-like carbon. This configuration has the advantage of being one of the hardest materials.

The articulating surface layer may be formed by a coating applied to a metallic or ceramic substrate, preferably like CoCrMo, CoCrMoC, Ti, TAN, TAV, Aluminium Oxide or Zirconium Oxide.

The surface layer may have a thickness between 0.5 µm and 800 µm, preferably between 2 µm and 25 µm.

In a further embodiment a bonding layer is disposed between the surface layer and the substrate. Since ADLC is significantly harder than the substrate, surface tension may result between. It has been found that the surface tension can be reduced by placing a bonding layer between the substrate and the surface layer (ADLC). The bonding layer can be a metal or a metal alloy, in particular it may comprise Niobium, Silizium, Tantalum or Gold or other biocompatible metals.

The bonding layer may have a thickness between 3 nm and 40 µm, preferably between 50 nm and 9 µm.

In a further embodiment the surface layer can be a multi-layer composite. The advantage of this design is a reduction of the surface tension through several "more elastic" layers from pure metals. The multi-layer composite may comprise the following sequence of single layers: (Substrate)-Ti—TiN—Ti—TiN.

The joint according to the invention may be part of an endojoint prosthesis, preferably for the hip, knee and shoulder, or of an intervertebral implant, preferably an intervertebral disk prosthesis.

A BRIEF DESCRIPTION OF THE DRAWINGS

Several embodiments of the invention will be described in the following by way of example and with reference to the accompanying drawings in which.

Figure 1:
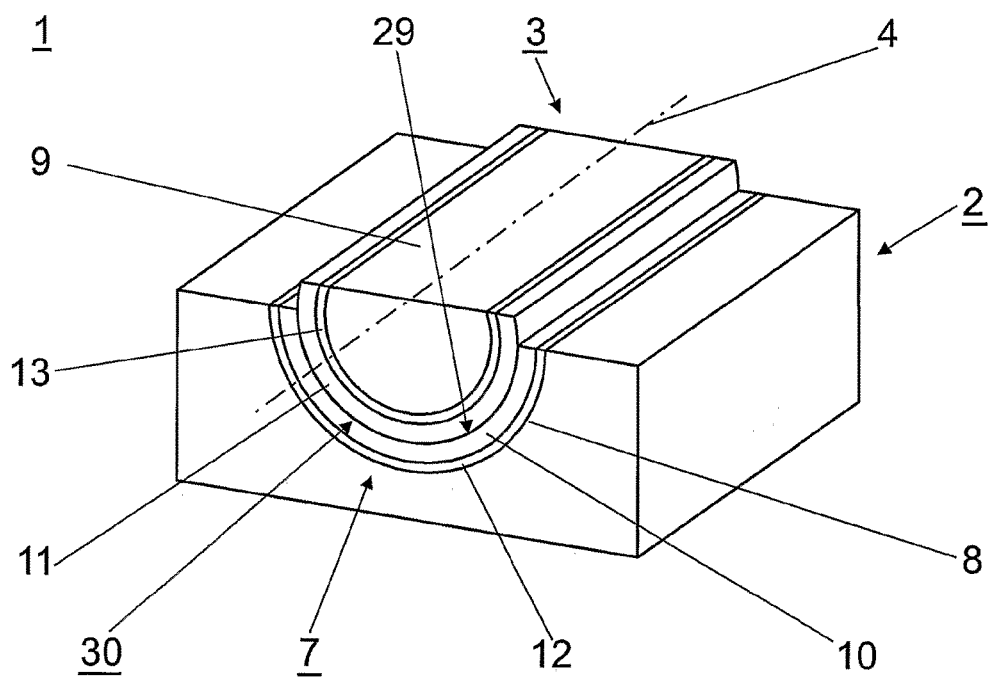
FIG. 1 shows a perspective view of the key functional members of a prosthetic joint according to the invention.

FIG. 1 schematically illustrates the key functional members of a prosthetic joint 1 according to the invention. The prosthetic joint 1 is configured as a uniaxial joint having an axis of rotation 4, schematizing e.g. a hinged knee prosthesis. The prosthetic joint 1 essentially comprises a first member 2 with a channel 7 coaxially penetrating the first member 2 and a second member 3 which is configured as an articular shaft 9. The first and second members 2;3 each are provided with an articulating surface layer 10;11 and a bonding layer 12;13 between the articulating surface layer 10;11 and the peripheral wall 8 of the channel 7, respectively the cylindrical surface of the articular shaft 9. The configuration of the prosthetic joint 1 with a convex sliding surface 29 at the articular shaft 9 and a concave sliding surface 30 at the peripheral wall 8 of the channel 7 solely permit a sliding relative motion between the first and second member 2;3.

Figure 2:
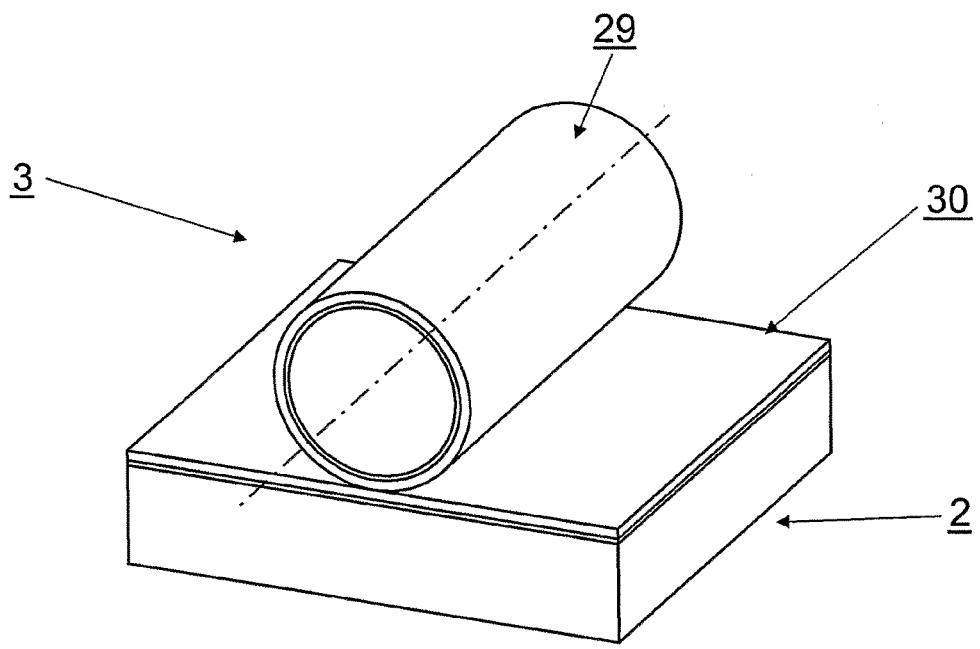
FIG. 2 shows a perspective view of the key functional members of another prosthetic joint according to the invention.
Figure 3:
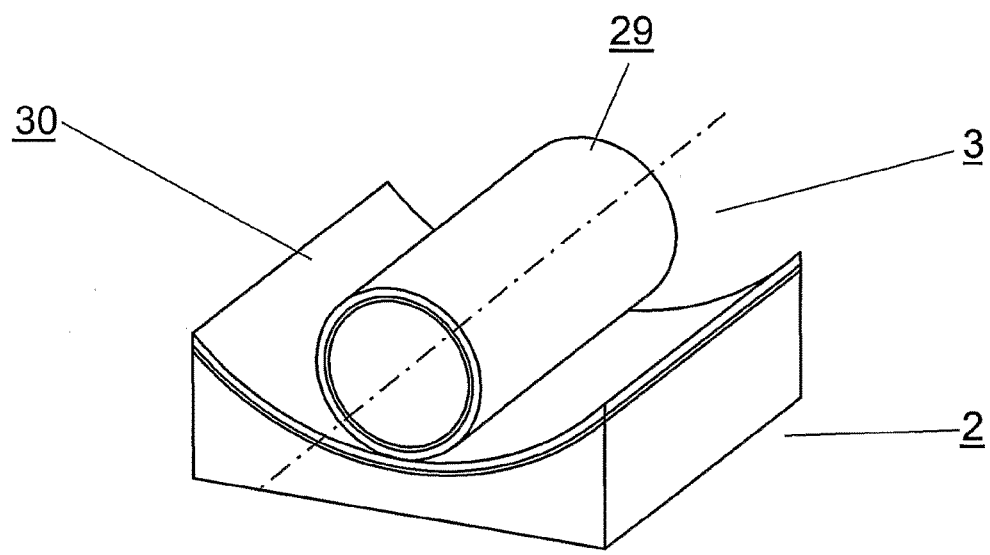
FIG. 3 shows a perspective view of the key functional members of yet another prosthetic joint according to the invention.
Figure 4:
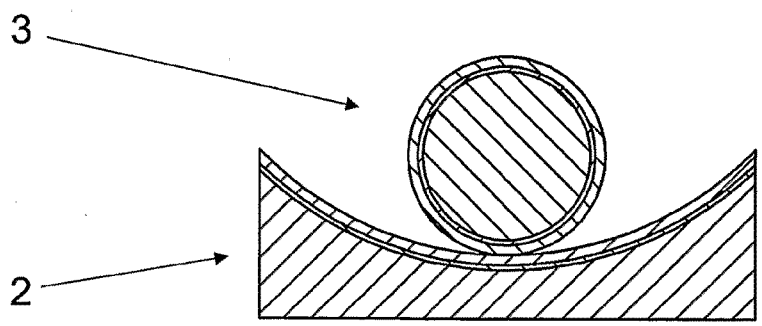
FIG. 4 shows a cross section of the prosthetic joint of FIG. 3.

FIGS. 2 to 4 schematically illustrate the key functional members of a further prosthetic joint 1 according to the invention, for example of a knee joint prosthesis of the surface replacement type. The embodiments in FIGS. 2 to 4 differ from the one shown in FIG. 1 solely in a plane (FIG. 4) respectively concave (FIGS. 5 and 6) configuration of the concave sliding surface 30 of the first member 2 and an articular shaft 9 having a circular cross section, whereby the radius of curvature of the concave sliding surface 30 of the first member 2 is greater than the radius of the convex sliding surface 29 of the articular shaft 9. This configuration of the first and second member 2;3 permits a superimposed sliding and rolling motion of the first and second member 2;3 relative to each other.

Figure 5:
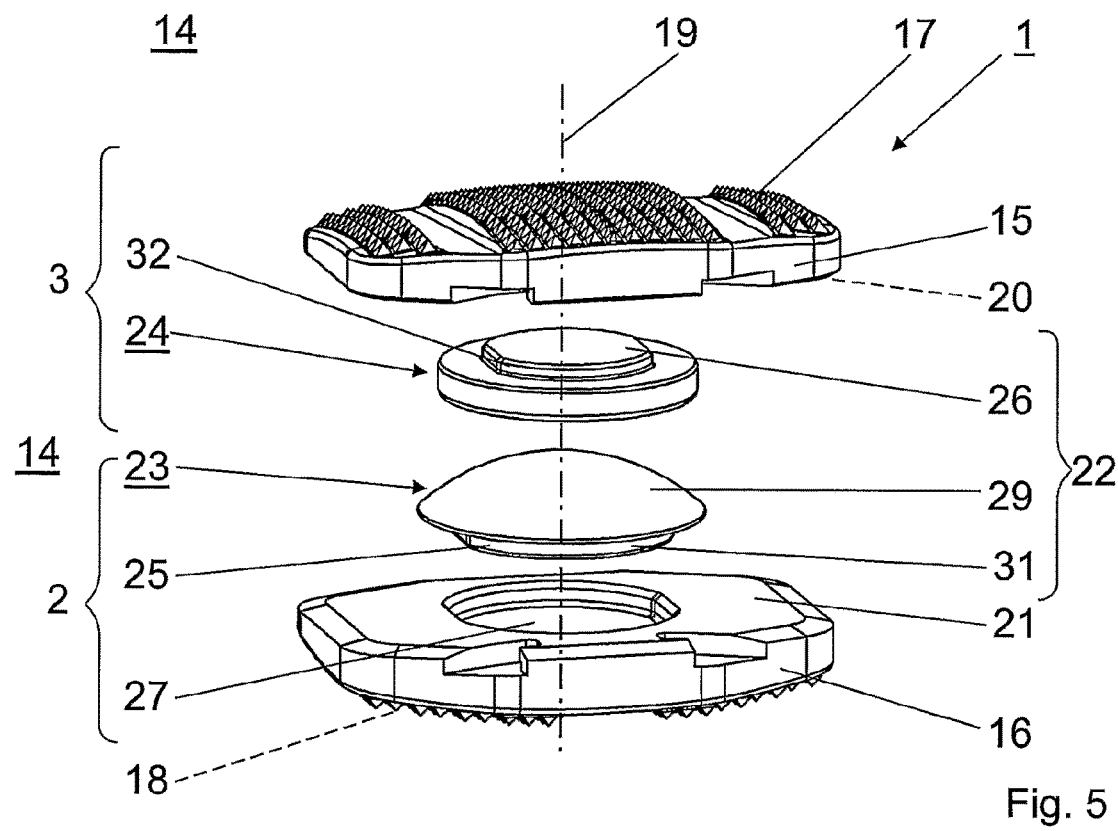
FIG. 5 shows an exploded view of an embodiment of the prosthetic joint according to the invention.
Figure 6:
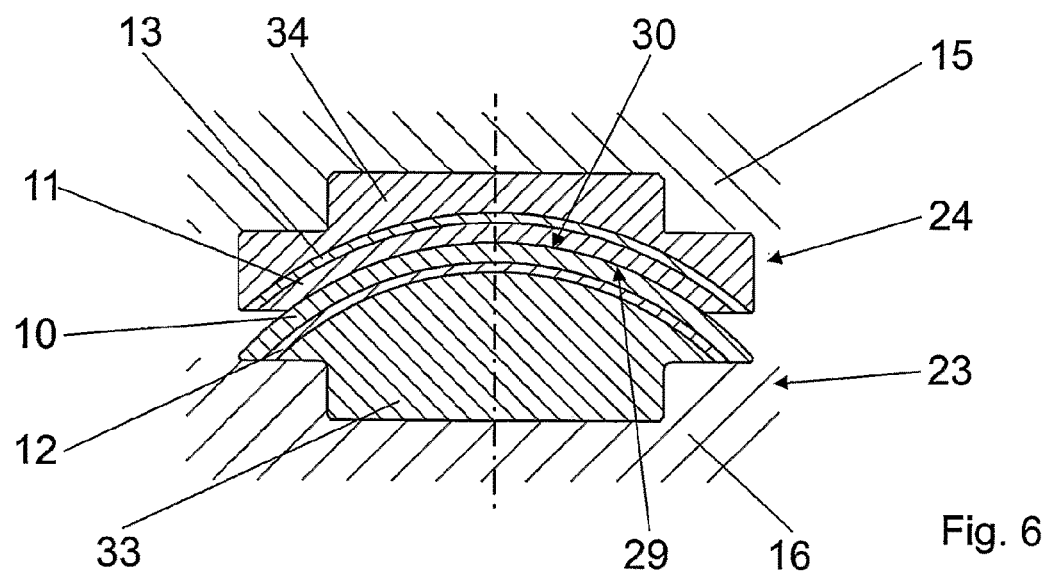
FIG. 6 shows a cross section of the embodiment of FIG. 5.

FIGS. 5 and 6 illustrate an embodiment of the prosthetic joint 1 in the form of an intervertebral implant 14, particularly an intervertebral disc prosthesis comprising an upper apposition member 15, a lower apposition member 16 and a ball-and-socket joint 22 articulatedly connecting said upper and lower apposition member 15;16. Opposite the ball-and-socket joint 22 the upper and lower apposition member 15;16 comprise an upper terminal surface 17, respectively a lower terminal surface 18, whereby said upper terminal surface 17 is configured for abutting the base plate of a first intervertebral body contacting the intervertebral implant 14 on top and said lower terminal surface 18 is configured for abutting the cover plate of a second intervertebral body contacting the intervertebral implant 14 at the bottom. The ball-and-socket joint 22 is a two-piece member having a spherical convex joint member 23, the convex sliding surface 29 of which is configured as a spherical cap with the central axis 19 of the intervertebral implant 14 intersecting the spherical cap at its apex. At the rear end 25 of the convex joint member 23 a first cylindrical section 31 is provided by means of which the convex joint member 23 may be fit into a corresponding first recess 27 in the intermediate surface 21 of the lower apposition member 16, which is arranged opposite to the lower terminal surface 18. Analogously, the rear end 26 of the concave joint member 24 comprises a second cylindrical section 32 by means of which the concave joint member 24 may be fit into a corresponding second recess 28 in the intermediate surface 20 of the upper apposition member 15 which is arranged opposite the upper terminal surface 17.

In this exemplary embodiment the first and second bonding layers 12;13 are metallic, have a thickness between 3 nanometer and 6 micrometer and are fixed at the respective first and second substrates 33;34 of the corresponding convex and concave joint members 23;24 by means of chemical vapor deposition technique whereas the first and second articulating surfaces 10;11 have a thickness between 2 and 30 micrometer and are applied by means of a plasma assisted chemical vapor deposition process.

The convex sliding surface 29 and the concave sliding surface 30 have the same radius, which permits a sliding motion of the convex sliding surface 29 relative to the concave sliding surface 30 when the ball-and-socket joint 22 is bent or stretched. Analogously, a sliding motion between the convex and concave sliding surface 29;30 is performed when the first and second member 2;3 of the prosthetic joint rotate relative to each other about the central axis 19.

What is claimed is:

1. An intervertebral implant comprising:
   an upper apposition member including an upper terminal surface sized and configured to abut a first vertebra, a lower surface opposite the upper terminal surface, and a first recess that extends into the lower surface;
   a lower apposition member including a lower terminal surface sized and configured to abut a second vertebra, an upper surface opposite the lower terminal surface, and a second recess that extends into the upper surface;
   a first substrate coupled to the upper apposition member, the first substrate including a first curved surface;
   an articulating surface layer and a bonding layer positioned between the articulating surface layer and the first curved surface, the articulating surface layer including a multi-layer composite, wherein the multi-layer composite includes a layer consisting of titanium and a layer consisting of titanium nitride adjacent the layer consisting of titanium; and
   a second substrate coupled to the lower apposition member, the second substrate including a second curved surface configured to movably contact the first curved surface so that the upper apposition member is moveable with respect to the lower apposition member.

2. The intervertebral implant of claim 1, wherein the articulating surface layer is a first articulating surface layer, the bonding layer is a first bonding layer, and the multi-layer composite is a first multi-layer composite; the intervertebral implant further comprising:
   a second articulating surface layer and a second bonding layer positioned between the second articulating surface layer and the second curved surface, the second articulating surface layer including a second multi-layer composite, wherein the second multi-layer composite includes a layer of titanium and a layer of titanium nitride adjacent the layer of titanium.

3. The intervertebral implant of claim 2, wherein the layer consisting of titanium is a first layer of titanium, the layer consisting of titanium nitride is a first layer of titanium nitride, and the first multi-layer composite includes a second layer of titanium and a second layer of titanium nitride adjacent the second layer of titanium.

4. The intervertebral implant of claim 3, wherein the second layer of titanium nitride is adjacent to the first layer of titanium.

5. The intervertebral implant of claim 2, wherein the first bonding layer comprises Niobium, Silizium, Tantalum or Gold.

6. The intervertebral implant of claim 5, wherein the second bonding layer comprises Niobium, Silizium, Tantalum or Gold.

7. The intervertebral implant of claim 1, wherein the first curved surface is concave, and the second curved surface is convex.

8. The intervertebral implant of claim 1, wherein the first curved surface is spherical.

9. The intervertebral implant of claim 8, wherein the second curved surface is spherical.

10. The intervertebral implant of claim 1, further comprising a joint member that is configured to be coupled to the upper apposition member, the joint member including the first substrate.

* * * * *